US00PP28603P3

(12) United States Plant Patent
Hansen

(10) Patent No.: US PP28,603 P3
(45) Date of Patent: Nov. 7, 2017

(54) ***DIANTHUS* PLANT NAMED 'CRANBERRY COCKTAIL'**

(50) Latin Name: ***Dianthus* hybrid**
Varietal Denomination: Cranberry Cocktail

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 65 days.

(21) Appl. No.: 14/998,557

(22) Filed: Jan. 19, 2016

(65) Prior Publication Data

US 2017/0208724 P1 Jul. 20, 2017

(51) Int. Cl.
*A01H 5/02* (2006.01)

(52) U.S. Cl.
USPC ..... Plt./277

(58) Field of Classification Search
USPC ..... Plt./277
See application file for complete search history.

*Primary Examiner* — Anne Grunberg

(57) ABSTRACT

A new and unique plant cultivar of perennial carnation or pinks, *Dianthus* plant named 'Cranberry Cocktail' with numerous, large, fully-double, fragrant flowers, on well-branched stems having up to 8 flowers per stem. Petals are hot magenta pink with coarse serrations. Plant has vigorous compact habit with gray-green foliage. The petals have a margin of light pink becoming nearly white. *Dianthus* 'Cranberry Cocktail' is tolerant of high temperatures and resists center die-out.

1 Drawing Sheet

Botanical denomination: *Dianthus* hybrid.
Cultivar designation: 'Cranberry Cocktail'.

BACKGROUND OF THE INVENTION

The present invention relates to the new and distinct cultivar of carnation or pinks from the genus *Dianthus* and given the cultivar name 'Cranberry Cocktail' previously known only internally by the breeder code 11-137-01. The new plant was the result of an intentional cross on May 19, 2011 by the inventor between *Dianthus* 'WP Passion' U.S. Plant Pat. No. 20,440 as the female or seed parent and 'Devon Flavia' U.S. Plant Pat. No. 15,903 as the male or pollen parent. Seeds of the cross were harvested Jun. 21, 2011. The new hybrid was first isolated from trials at a wholesale perennial nursery in Zeeland, Mich. during the summer of 2012 as a single seedling clone and given the breeder number 11-137-01 during the remaining evaluation processes. *Dianthus* 'Cranberry Cocktail' has been asexually propagated at the same nursery in Zeeland, Mich. since 2012 using traditional shoot tip cutting procedures and found to reproduce plants that are identical and exhibit all the characteristics of the original plant.

No plants of *Dianthus* 'Cranberry Cocktail' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventor.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant.

Comparing the new plant with the female parent, 'WP Passion', the new plant has a more mounded and less upright habit, larger flowers with more petals, and the petal color is more red-purple than red. Compared to the male parent, 'Devon Flavia', the new plant is more broad in habit, has larger flowers with more petals and the petal color is a deeper hot magenta pink. Other similar *Dianthus* include: 'Waterloo Sunset' U.S. Plant Pat. No. 21,080, and 'Starlette' U.S. Plant Pat. No. 21,438. *Dianthus* 'Cranberry Cocktail' produces more flowers per peduncle than all of the above, with large flowers of hot magenta pink.

Table 1 below shows further comparisons.

TABLE 1

| CULTIVAR | Leaf color | Flower color | Habit | Size (H × W) |
|---|---|---|---|---|
| 'Cranberry Cocktail' | gray-green | hot magenta-pink | mounded | 28 cm × 30 cm |
| 'Devon Flavia' | blue-green | sugar pink | compact | 30 cm × 15 cm |
| 'Waterloo Sunset' | gray-green | magenta-red | upright | 55 cm × 28 cm |
| 'WP Passion' | gray-green | deep red | upright | 35 cm × 25 cm |
| 'Starlette' | gray-green | raspberry-pink | compact | 28 cm × 22 cm |

| CULTIVAR | # Petals | Ground petal color | Petal band |
|---|---|---|---|
| 'Cranberry Cocktail' | 40-54 | 61A-61B | none |
| 'Devon Flavia' | 25-40 | 62B | reddish-purple |
| 'Waterloo Sunset' | 20-40 | 63B | 61C |
| 'WP Passion' | 20-30 | 46A, 53A | none |
| 'Starlette' | 15-20 | 70B | none |

*Dianthus* 'Cranberry Cocktail' is distinct from its parents and all other *Dianthus* known to the applicant in the following combined traits:

1. Fully-double flowers with numerous overlapping petals of hot magenta pink.
2. Petals having a serrated apex.
3. Numerous flowers per peduncle with many flowers on heavily branched stems.
4. Large flower size producing a sweetly spicy fragrance.
5. High heat tolerance with no vernalization required for flower production.
6. Floriferous, vigorous, with compact habit and finely-textured gray-green foliage.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
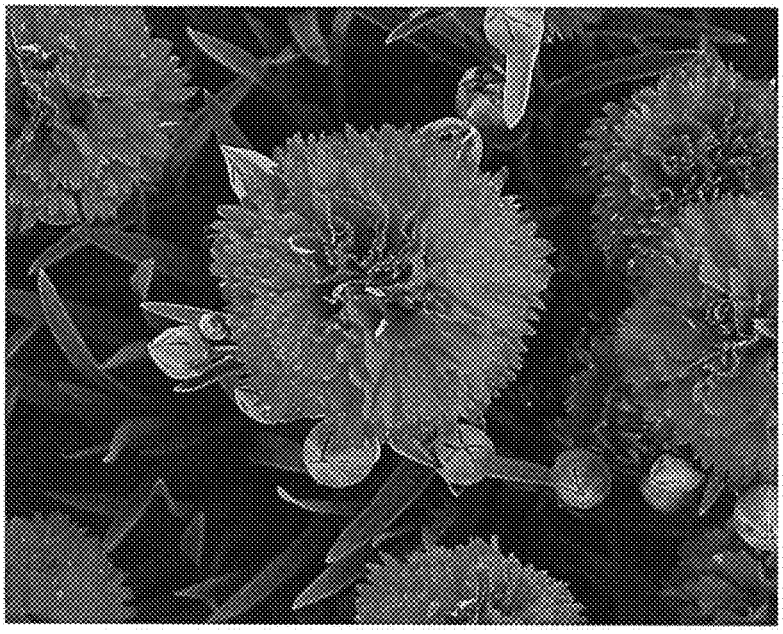
FIG. 1 s a close-up of the flowers and buds.
Figure 2:
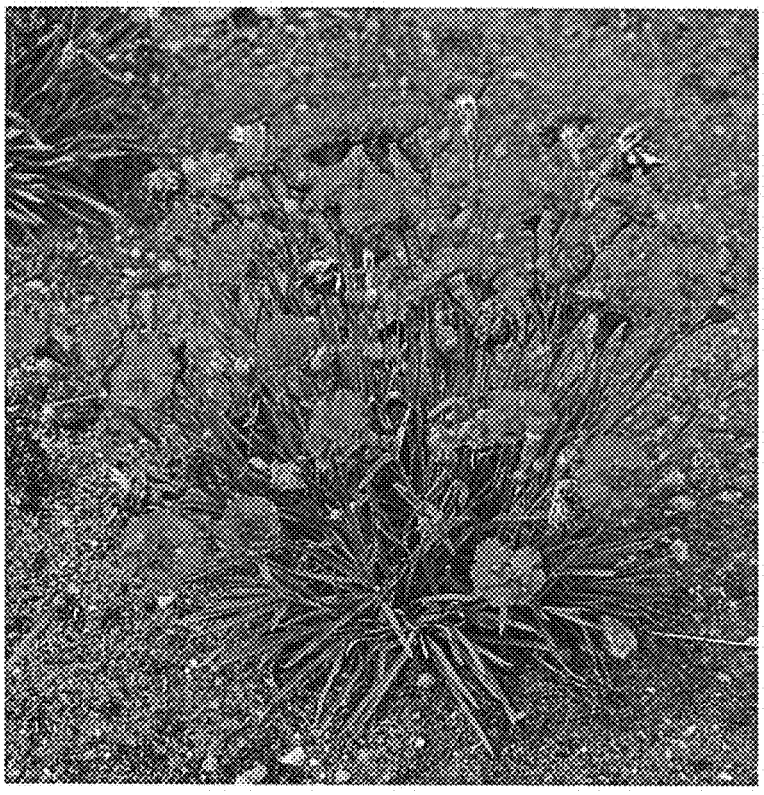
FIG. 2 shows the habit of the plant in mid-season flowering.

The following detailed description of the new plant is based on observations of two-year old plants in greenhouse-grown containers at a nursery in Zeeland, Mich. with light shade, supplemental watering, light additions of fertilizer and free of other plant growth regulators. All color usage is in accordance with the 2001 edition of The Royal Horticultural Colour Chart except where common dictionary terms are used.

Botanical classification: *Dianthus* hybrid.

Parentage: 'WP Passion' U.S. Plant Pat. No. 20,440 as the female or seed parent and 'Devon Flavia' U.S. Plant Pat. No. 15,903 as the male or pollen parent.

Plant description:

*Habit.*—Caespitose, herbaceous, evergreen perennial; stems and peduncles branched, erect to arching with weight, number and size of flowers; height of foliage about 16.0 cm and about 30.0 cm across; height in flower is about 28.0 cm.

*Root system.*—Fine, fibrous; color nearest RHS 155D.

*Vigor.*—Good, spring planted plugs finish in 3.8 liter pots in seven to eight weeks.

Foliage:

*Leaf type.*—Simple, linear, opposite, decussate, sessile, glabrous, glaucous on adaxial and abaxial; margin entire to microscopically serrulate; acute apex; base decurrent, adpressed along stem and slightly perfoliate; no fragrance detected.

*Leaf dimensions.*—To about 9.5 cm long and about 5.0 mm wide, average about 6.8 cm long and 4.0 mm wide.

*Leaf color.*—Young expanding leaves abaxial and adaxial between RHS N138A and RHS N138B; mature adaxial nearest RHS 139A and abaxial between RHS N138A and RHS 139A.

*Venation.*—Not pronounced; obscurely pinnate, coloration same as that of leaf top and bottom.

Stems: Beginning erect and becoming arching with development of flowers; terete, glabrous, glaucous, branching at alternate nodes; about 16 per plant.

*Stem size.*—About 20.0 cm long and about 4.0 mm wide at base.

*Stem color.*—Nearest RHS N138C.

*Branching.*—Numerous; typically alternate, from upper and lower leaf axils; about 12 per main stem and about 200 per plant; branch size average about 6.5 cm at time of initial flowering.

*Nodes.*—About 4.0 mm across; color nearest RHS 142D.

*Internodes.*—Average about 1.8 cm apart depending on growing temperature, shorter in cooler conditions.

Inflorescence:

*Type.*—Terminal, cymose; salverform; actinomophic; completely double.

*Attitude.*—Upright to slightly arching.

*Dimension.*—About 6.0 cm across and extending about 23.0 mm above calyx tube.

*Flowers per stem.*—Four to eight.

*Pedicel.*—Glaucous, glabrous, terete.

*Pedicel size.*—Terminal flower about 3.5 mm long and about 2.0 mm diameter; other flowers average about 17.0 mm long and 1.5 mm diameter.

*Pedicel color.*—Nearest RHS N138D.

*Flower bud one day prior to opening.*—Glaucous, glabrous, ellipsoid with rounded apex and rounded base.

*Flower bud size.*—One day prior to opening — about 2.8 cm long and about 1.4 cm wide; while petals still enclosed in calyx — about 2.0 cm long and about 12.0 mm wide.

*Flower bud color.*—While still enclosed in calyx — between RHS 137A and RHS N138A at apex and RHS 145A at base; with petals exposed and still tight — petals nearest RHS 61A at apex and next to calyx nearest RHS 155D and calyx same as while petals still enclosed in calyx.

*Flower period.*—Beginning late spring and repeating in early fall; effective about four weeks per flowering season.

*Flower fragrance.*—Light, sweet spicy, clove-like.

*Flower lasting quality.*—About ten days on or cut from plant.

*Petals.*—Glabrous; 40 to 54 per flower, with as many as ten petals split in the distal 42.0 to 40.0 mm of the claw and the limb with distal claw separated; consisting of a rounded blade or limb and a claw, outer petals with broader and more rounded limb; limb and claw combined are obovate with long tapered claw; apex and margin with coarse dentations 3.0 mm deep; limb bent outwardly in distal 18.0 mm to nearly a ninety degree angle; claw tapering to truncate base about 1.0 mm across; persistent.

*Petal color.*—Petal limb abaxial base nearest RHS 64D, adaxial base nearest RHS N66D; abaxial and adaxial main limb between RHS 61A and RHS 61B with slightly darker veins of nearest RHS 61A; petal claw abaxial and adaxial nearest RHS 145C with 2.0 mm transition between claw and limb lighter than RHS 155D.

*Petal dimension.*—Size to about 44.0 mm long and 25.0 mm across at widest part of limb, average about 40.0 mm long and about 20.0 mm wide; claw portion average about 18.0 mm long and about 1.0 mm at base; limb portion average about 22.0 mm long and 20.0 mm wide.

*Calyx.*—Glabrous, glaucous; margins entire; consisting of five sepals with acute apex and fused base forming five-toothed corolla tube fused in proximal 1.7 cm;

individually about 2.2 cm long and about 0.7 cm across; campanulate to about 22.0 mm long and about 12.0 mm in diameter.

*Calyx color.*—Abaxial between RHS 137A and RHS N138A at apex and RHS 145A at base; adaxial between RHS 145B and RHS 146D; 0.5 mm wide margins both adaxial and abaxial nearest RHS 158B.

*Peduncle.*—Glabrous, glaucous, terete, about 25.0 cm long and about 4.0 mm diameter at base.

*Peduncle color.*—Nearest RHS N138C.

*Bracts.*—Two, opposite, glaucous, glabrous; sessile margin entire, broadly obtuse to deltoid with broadly acute apex; about 9.0 mm long and 10.0 mm wide.

*Bract color.*—Abaxial and adaxial distally nearest RHS 139A and proximally nearest RHS 145B; margins of about 0.5 mm both sides nearest RHS 158B.

*Bracteoles.*—Two; glaucous, glabrous; margins entire; opposite and at 90 degrees offset from and frequently just inside bracts; broadly obtuse to deltoid with broadly acute apex; sessile bases joined at stem; about 8.0 mm long and 8.0 mm wide.

*Bracteoles color.*—Abaxial and adaxial distally nearest RHS 139A, adaxial and abaxial basal portion between RHS 145B and RHS 145C, margins transparent.

*Androecium.*—Up to twelve stamens, typically not fully formed. Filaments: variable in length from 0.8 cm to 2.4 cm long, less than about 1.0 mm diameter; color nearest RHS 155A in basal three quarters and lighter than RHS 72D in distal one quarter. Anther: rare; sagittate to irregular, dorsifixed; typically not fully formed; about 2.0 mm long and about 1.0 mm wide; color nearest RHS186D. Pollen: not observed.

*Gynoecium.*—Style: typically split in two just above ovary. Pistil: glabrous abaxial surface and puberulent adaxial surface; irregularly curled; about 2.0 cm long and about 1.0 mm diameter; color much lighter than RHS 72D only on adaxial side. Stigma: puberulent; about 1.0 cm long and 1.0 mm wide; irregularly curled; color nearest RHS 72D. Ovary: superior; ellipsoid-shaped; about 9.0 mm long and 5.0 mm wide; surface texture glabrous and nitid; color between RHS 145B and RHS 145C.

Fruit: Capsule; ovoid to cylindrical; opening by 4 teeth; about 2 cm long and 8.5 mm diameter; color between RHS 164B and RHS 164A when dried.

Seed: Not observed.

Disease resistance: The new plant is resistance to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct *Dianthus* plant named 'Cranberry Cocktail' essentially as herein described and illustrated.

* * * * *